(12) United States Patent
Shelly et al.

(10) Patent No.: US 9,744,322 B2
(45) Date of Patent: Aug. 29, 2017

(54) AUTOMATIC PRESSURE TITRATION

(71) Applicant: KONINKLIJKE PHILIPS N.V., Eindhoven (NL)

(72) Inventors: Benjamin Irwin Shelly, Pittsburgh, PA (US); Michael Thomas Kane, Harrison City, PA (US); Gregory Delano Matthews, Pittsburgh, PA (US); Heather Dawn Ressler, Blairsville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 51 days.

(21) Appl. No.: 14/717,045

(22) Filed: May 20, 2015

(65) Prior Publication Data

US 2015/0250964 A1  Sep. 10, 2015

Related U.S. Application Data

(63) Continuation of application No. 13/202,331, filed as application No. PCT/IB2010/050295 on Jan. 22, 2010, now Pat. No. 9,056,172.

(Continued)

(51) Int. Cl.
*A61M 16/00* (2006.01)
*A61M 16/06* (2006.01)

(52) U.S. Cl.
CPC ........ *A61M 16/0069* (2014.02); *A61M 16/00* (2013.01); *A61M 16/0003* (2014.02);
(Continued)

(58) Field of Classification Search
CPC .. A61M 16/00; A61M 16/06; A61M 16/0858; A61M 16/0066; A61M 16/0875; A61M 16/0069; A61M 16/0003; A61M 16/0045; A61M 16/0051; A61M 16/0057; A61M 16/0072; A61M 16/0075; A61M 16/0431; A61M 16/0633; A61M 16/0644; A61M 16/0666; A61M 16/0677; A61M 16/0683; A61M 16/08; A61M 16/0816;
(Continued)

(56) References Cited

U.S. PATENT DOCUMENTS 5,245,995 A  9/1993  Sullivan et al.
5,259,373 A  11/1993  Gruenke et al.
(Continued)

FOREIGN PATENT DOCUMENTS

CN  1431886 A  7/2003
JP  2009506833 A  2/2009
(Continued)

*Primary Examiner* — Annette Dixon
(74) *Attorney, Agent, or Firm* — Michael W. Haas

(57) ABSTRACT

A pressure support methodology and system that utilizes at least two, and possibly all three, of information relating to (i) airway patency, i.e., the degree to which the patient's airway is open, (ii) the primary cause of the current sleep disordered breathing event, and (iii) the patient's response to previous pressure changes to automatically titrate pressure when presented with a sleep disordered breathing event. In another embodiment, pressure may be automatically titrated based solely on the primary cause of the sleep disordered breathing event.

10 Claims, 7 Drawing Sheets

Related U.S. Application Data

(60) Provisional application No. 61/155,351, filed on Feb. 25, 2009.

(52) U.S. Cl.
CPC ......... *A61M 16/06* (2013.01); *A61M 16/0006* (2014.02); *A61M 2016/003* (2013.01); *A61M 2016/0027* (2013.01); *A61M 2205/3334* (2013.01); *A61M 2205/50* (2013.01); *A61M 2205/52* (2013.01)

(58) Field of Classification Search
CPC .............. A61M 16/0883; A61M 16/10; A61M 16/1045; A61M 16/12; A61M 16/16; A61M 16/161; A61M 16/204; A61M 16/205; A61M 16/209; A61M 2016/0018; A61M 2016/0021; A61M 2016/0027; A61M 2016/003; A61M 2016/0033; A61M 2016/0036; A61M 2016/0039; A61M 2016/0042; A61M 2016/102; A61M 2016/1025; A61M 2016/103; A61M 2202/0208; A61M 2202/0225; A61M 2205/054; A61M 2205/15; A61M 2205/16; A61M 2205/18; A61M 2205/3303; A61M 2205/3306; A61M 2205/3317; A61M 2205/3324; A61M 2205/3334; A61M 2205/3355; A61M 2205/3358; A61M 2205/3368; A61M 2205/3375; A61M 2205/3523; A61M 2205/3553; A61M 2205/3561; A61M 2205/3569; A61M 2205/3576; A61M 2205/3584; A61M 2205/3592; A61M 2205/50; A61M 2205/502; A61M 2205/52; A61M 2205/702; A61M 2205/8206; A61M 2210/0618; A61M 2230/00; A61M 2230/005; A61M 2230/04; A61M 2230/06; A61M 2230/08; A61M 2230/10; A61M 2230/14; A61M 2230/18; A61M 2230/202; A61M 2230/205; A61M 2230/208; A61M 2230/30; A61M 2230/40; A61M 2230/42; A61M 2230/43; A61M 2230/432; A61M 2230/435; A61M 2230/46; A61M 2230/50; A61M 2230/60; A61B 5/00; A61B 5/0002; A61B 5/002; A61B 5/0022; A61B 5/0031; A61B 5/0205; A61B 5/02055; A61B 5/021; A61B 5/0215; A61B 5/02405; A61B 5/02416; A61B 5/0408; A61B 5/0421; A61B 5/0422; A61B 5/0456; A61B 5/0464; A61B 5/0472; A61B 5/0476; A61B 5/0478; A61B 5/0488; A61B 5/0492; A61B 5/0496; A61B 5/053; A61B 5/0538
USPC ............ 128/200.24, 204.18, 204.21, 204.23, 128/203.14, 204.22, 204.26, 206.21, 128/206.24, 207.11, 207.18; 600/300, 600/310, 323, 324, 335, 364, 483, 484, 600/500, 509, 529, 532, 534, 538, 544, 600/546, 595
See application file for complete search history.

(56) References Cited

U.S. PATENT DOCUMENTS

| | | |
|---|---|---|
| 5,295,490 A | 3/1994 | Dodakian |
| 5,335,654 A | 8/1994 | Rapoport |
| 5,398,682 A * | 3/1995 | Lynn .................. A61B 5/14551 128/204.18 |
| 5,458,137 A | 10/1995 | Axe et al. |
| 5,490,502 A | 2/1996 | Rapoport et al. |
| 5,535,738 A | 7/1996 | Estes et al. |
| 5,535,739 A | 7/1996 | Rapoport et al. |
| 5,549,106 A | 8/1996 | Gruenke et al. |
| 5,605,151 A | 2/1997 | Lynn |
| 5,645,053 A | 7/1997 | Remmers et al. |
| 5,704,345 A | 1/1998 | Berthon-Jones |
| 5,794,615 A | 8/1998 | Estes |
| 5,797,852 A | 8/1998 | Karakasoglu et al. |
| 5,803,066 A | 9/1998 | Rapoport et al. |
| 5,845,636 A | 12/1998 | Gruenke et al. |
| 5,961,447 A | 10/1999 | Raviv et al. |
| 6,029,665 A | 2/2000 | Berthon-Jones |
| 6,058,747 A | 5/2000 | Doyle et al. |
| 6,085,747 A | 7/2000 | Axe |
| 6,105,575 A | 8/2000 | Estes et al. |
| 6,138,675 A | 10/2000 | Berthon-Jones |
| 6,142,950 A | 11/2000 | Allen et al. |
| 6,165,133 A | 12/2000 | Rapoport et al. |
| 6,368,287 B1 | 4/2002 | Hadas |
| 6,532,959 B1 | 3/2003 | Berthon-Jones |
| 6,609,517 B1 | 8/2003 | Estes et al. |
| 6,752,151 B2 | 6/2004 | Hill |
| 6,932,084 B2 | 8/2005 | Estes et al. |
| 7,118,536 B2 | 10/2006 | Haberland et al. |
| 7,168,429 B2 | 1/2007 | Matthews et al. |
| 7,320,320 B2 | 1/2008 | Berthon-Jones |
| 7,717,110 B2 | 5/2010 | Kane |
| 7,942,824 B1 * | 5/2011 | Kayyali .................. A61B 5/021 128/204.23 |
| 8,545,416 B1 * | 10/2013 | Kayyali .................. A61B 5/085 128/204.23 |
| 2005/0061320 A1 | 3/2005 | Lee et al. |
| 2005/0268912 A1 * | 12/2005 | Norman ............ A61M 16/0051 128/204.23 |
| 2006/0042627 A1 * | 3/2006 | MacMillan ........... A61M 16/00 128/204.22 |
| 2006/0070624 A1 | 4/2006 | Kane et al. |
| 2006/0070625 A1 * | 4/2006 | Ayappa ............. A61M 16/0051 128/204.23 |
| 2008/0243016 A1 * | 10/2008 | Liao ..................... A61B 5/0205 600/532 |

FOREIGN PATENT DOCUMENTS

| | | |
|---|---|---|
| WO | WO9728838 A1 | 8/1997 |
| WO | WO2006099670 | 9/2006 |
| WO | WO2007027888 A2 | 3/2007 |

\* cited by examiner

AUTOMATIC PRESSURE TITRATION

This patent application is a Continuation of U.S. patent application Ser. No. 13/202,331, filed Aug. 19, 2011, which claims the priority benefit under 35 U.S.C. §119(e) of U.S. Provisional Application No. 61/155,351 filed on Feb. 25, 2009, the contents of which are herein incorporated by reference.

The present invention relates to airway pressure support systems, and, more particularly, to a methodology for automatically titrating the pressure for patients, particularly where sleep disordered breathing (SDB) presents complex symptoms.

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

Devices are known that attempt to detect apneas and hypopneas to determine in real time whether a patient suffers from a sleep apnea syndrome. Examples of conventional apnea/hypopnea detection devices are described in U.S. Pat. No. 5,295,490 to Dodakian; U.S. Pat. No. 5,605,151 to Lynn; U.S. Pat. No. 5,797,852 to Karakasoglu et al.; U.S. Pat. No. 5,961,447 to Raviv et al.; U.S. Pat. No. 6,142,950 to Allen et al.; U.S. Pat. No. 6,165,133 to Rapoport et al.; U.S. Pat. No. 6,368,287 to Hadas.

It is further well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing. Thus, the effectiveness of treating a patient via an auto-titration type of pressure support system can depend to a great extent on the accurate detection of apneas and/or hypopneas.

Examples of conventional auto-titration pressure support system are disclosed in U.S. Pat. No. 5,245,995 to Sullivan et al.; U.S. Pat. Nos. 5,259,373; 5,549,106, and 5,845,636 all to Gruenke et al.; U.S. Pat. Nos. 5,458,137 and 6,058,747 both to Axe et al.; U.S. Pat. Nos. 5,704,345; 6,029,665, and 6,138,675 all to Berthon-Jones; U.S. Pat. No. 5,645,053 to Remmers et al.; and U.S. Pat. Nos. 5,335,654; 5,490,502, 5,535,739, and 5,803,066 all to Rapoport et al. All of these conventional pressure support systems, with the possible exception of U.S. Pat. No. 5,645,053 to Remmers et al., are reactive to the patient's monitored condition. That is, once a condition occurs that indicates abnormal breathing, the system alters the pressure support to treat this condition.

The spectrum of disease states that cause and affect sleep disordered breathing is as far ranging as it is complicated. Complex patients, for example, patients with Cheyne-Stokes Respiration, Opioid-Induced Central Sleep Apnea, CPAP-Emergent Sleep Apnea, etc., are currently treated with either BiPAP S/T devices (BiPAP devices with fixed backup rates) or with ASV devices, as described for example in U.S. Pat. No. 6,532,959 to Berthon-Jones, U.S. Pat. No. 6,752,151 to Hill, and U.S. patent application Ser. No. 11/235,520 (publication no. 2006-0070624-A1) to Kane. While complex patients are often treated quite adequately on BiPAP S/T devices and ASV devices, both types of devices require a physician to titrate a portion of the therapy (EPAP and IPAP in the case of BiPAP S/T devices and just EPAP in the case of ASV devices). Most typically, EPAP is titrated to reduce obstructive activity, especially obstructive apneas and severe obstructive hypopneas. IPAP and backup rate are used (mostly automatically in the ASV device) to treat the remaining mild obstructive activity and the central activity, e.g., central apneas and hypopneas.

The physician interaction is required for titration of EPAP because, even with a smarter device (such as ASV), titrating EPAP on a complex patient is a difficult task that requires making decisions concerning the type of events that are being incurred, etc. Mistakes in titrating the pressure can are made in this process, due, for example, to human error on the part of sleep technicians doing the work. While some physicians are able to perform the titration correctly, many have difficulty. Thus, there is a need for an improved methodology for titrating pressure support systems that can, for example, more effectively treat patients that are regarded as complex. More specifically, there is a need for an improved methodology for automating the difficult process of titrating EPAP (or CPAP on an AutoCPAP device) on a complex patient.

In one embodiment, a method of providing pressure support to a patient is provided that includes detecting an occurrence of a sleep disordered breathing event in the patient, and, in response to the detecting, titrating a pressure of a flow of gas provided to the patient based on at least two of: (i) a determined patency of an airway of the patient, (ii) a determined cause of the sleep disordered breathing event, and (iii) a determined responsiveness of the patient to previous pressure changes in the flow of gas provided to the patient.

In one particular embodiment, the titrating comprises (i) performing no titration of the pressure if the airway is determined to be open, (ii) increasing the pressure if the airway is determined to be closed and if the sleep disordered breathing event is determined to not be centrally-mediated, (iii) performing one of (a) decreasing the pressure or (b) not changing the pressure if the airway is determined to be closed, if the sleep disordered breathing event is determined to be centrally-mediated, and if the determined responsiveness is non-responsive to the previous pressure changes in the flow of gas provided to the patient, and (iv) increasing the pressure if the airway is determined to be closed, if the sleep disordered breathing event is determined to be centrally-mediated, and if the determined responsiveness is responsive to the previous pressure changes in the flow of gas provided to the patient.

In another particular embodiment, the titrating is based only on the determined patency of the airway of the patient and the determined responsiveness of the patient to previous pressure changes in the flow of gas provided to the patient, and wherein the titrating includes (i) performing no titration of the pressure if the airway is determined to be open, (ii) performing one of (a) decreasing the pressure or (b) not changing the pressure if the airway is determined to be closed and if the determined responsiveness is non-responsive to the previous pressure changes in the flow of gas provided to the patient, and (iii) increasing the pressure if the airway is determined to be closed and if the determined responsiveness is responsive to the previous pressure changes in the flow of gas provided to the patient.

In still another particular embodiment, the titrating is based only on the determined patency of the airway of the patient and the determined cause of the sleep disordered breathing event, and wherein the titrating includes (i) performing no titration of the pressure if the airway is determined to be open, (ii) increasing the pressure if the airway is determined to be closed and if the sleep disordered breathing event is determined to not be centrally-mediated, and (iii) increasing the pressure to no more than a predetermined threshold if the airway is determined to be closed and if the sleep disordered breathing event is determined to be centrally-mediated.

In still another particular embodiment, the titrating is based only on the determined cause of the sleep disordered breathing event and the determined responsiveness of the patient to previous pressure changes in the flow of gas provided to the patient, and wherein the titrating comprises (i) increasing the pressure if the sleep disordered breathing event is determined to not be centrally-mediated, (ii) performing one of (a) decreasing the pressure or (b) not changing the pressure if the sleep disordered breathing event is determined to be centrally-mediated and if the determined responsiveness is non-responsive to the previous pressure changes in the flow of gas provided to the patient, and (iii) increasing the pressure if the sleep disordered breathing event is determined to be centrally-mediated and if the determined responsiveness is responsive to the previous pressure changes in the flow of gas provided to the patient.

The method may further include, in response to the detecting, determining the determined patency of the airway of the patient by providing a test pressure increase of predetermined amplitude to the patient, evaluating a degree of flow response to the test pressure increase and comparing a volume of the flow response to a predetermined volume threshold, wherein if the volume is greater than the predetermined volume threshold the airway is determined to be open and if the volume is less than or equal to the predetermined volume threshold the airway is determined to be closed. Alternatively, the method may further include, in response to the detecting, determining the determined patency of the airway of the patient by providing a pressure increase having an independently-controlled magnitude to the patient, measuring a flow response to the pressure increase, and determining whether the airway is open or closed based on the flow response to the pressure increase. In this latter embodiment, the determining whether the airway is open or closed based on the flow response to the pressure increase comprises computing a volume of the flow response, and comparing the volume to a predetermined volume threshold that is determined by a magnitude of the pressure increase, wherein if the volume is greater than the predetermined volume threshold the airway is determined to be open and if the volume is less than or equal to the predetermined volume threshold the airway is determined to be closed.

A pressure support system is also provided that includes a pressure generating system adapted to produce a flow of gas, a patient circuit operatively coupled to the pressure generating system to deliver the flow of gas to an airway of a patient, and a controller operatively coupled to the pressure generating system, the controller being adapted to control a pressure of the flow of gas by detecting an occurrence of a sleep disordered breathing event in the patient, and in response to the detecting, titrating the pressure of the flow of gas provided to the patient based on at least two of: (i) a determined patency of an airway of the patient, (ii) a determined cause of the sleep disordered breathing event, and (iii) a determined responsiveness of the patient to previous pressure changes in the flow of gas provided to the patient. Furthermore, the controller may be adapted to perform the various embodiments of the method just described.

According to an alternative embodiment, a method of providing pressure support to a patient is provided that includes detecting an occurrence of a sleep disordered breathing event in the patient, and in response to the detecting, titrating a pressure of a flow of gas provided to the patient based on a determined cause of the sleep disordered breathing event. The method may further include determining whether the sleep disordered breathing event is centrally-mediated, wherein the titrating comprises titrating the pressure of the flow of gas in a first manner, such as not changing the pressure (or not increasing the pressure above a preset threshold e.g. 10 cm H2O), if the sleep disordered breathing event is determined to be centrally-mediated and titrating the pressure of the flow of gas in a second manner different than the first manner, such as increasing the pressure (e.g. 1 cm H2O), if the sleep disordered breathing event is determined to not be centrally-mediated.

In yet another embodiment, a pressure support system is provided that includes a pressure generating system adapted to produce a flow of gas, a patient circuit operatively coupled to the pressure generating system to deliver the flow of gas to an airway of a patient, and a controller operatively coupled to the pressure generating system, the controller being adapted to control a pressure of the flow of gas by detecting an occurrence of a sleep disordered breathing event in the patient, and in response to the detecting, titrating the pressure of the flow of gas based on a determined cause of the sleep disordered breathing event. The controller may be further adapted to determine whether the sleep disordered breathing event is centrally-mediated, wherein the titrating includes titrating the pressure of the flow of gas in a first manner if the sleep disordered breathing event is determined to be centrally-mediated and titrating the pressure of the flow of gas in a second manner different than the first manner if the sleep disordered breathing event is determined to not be centrally-mediated.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
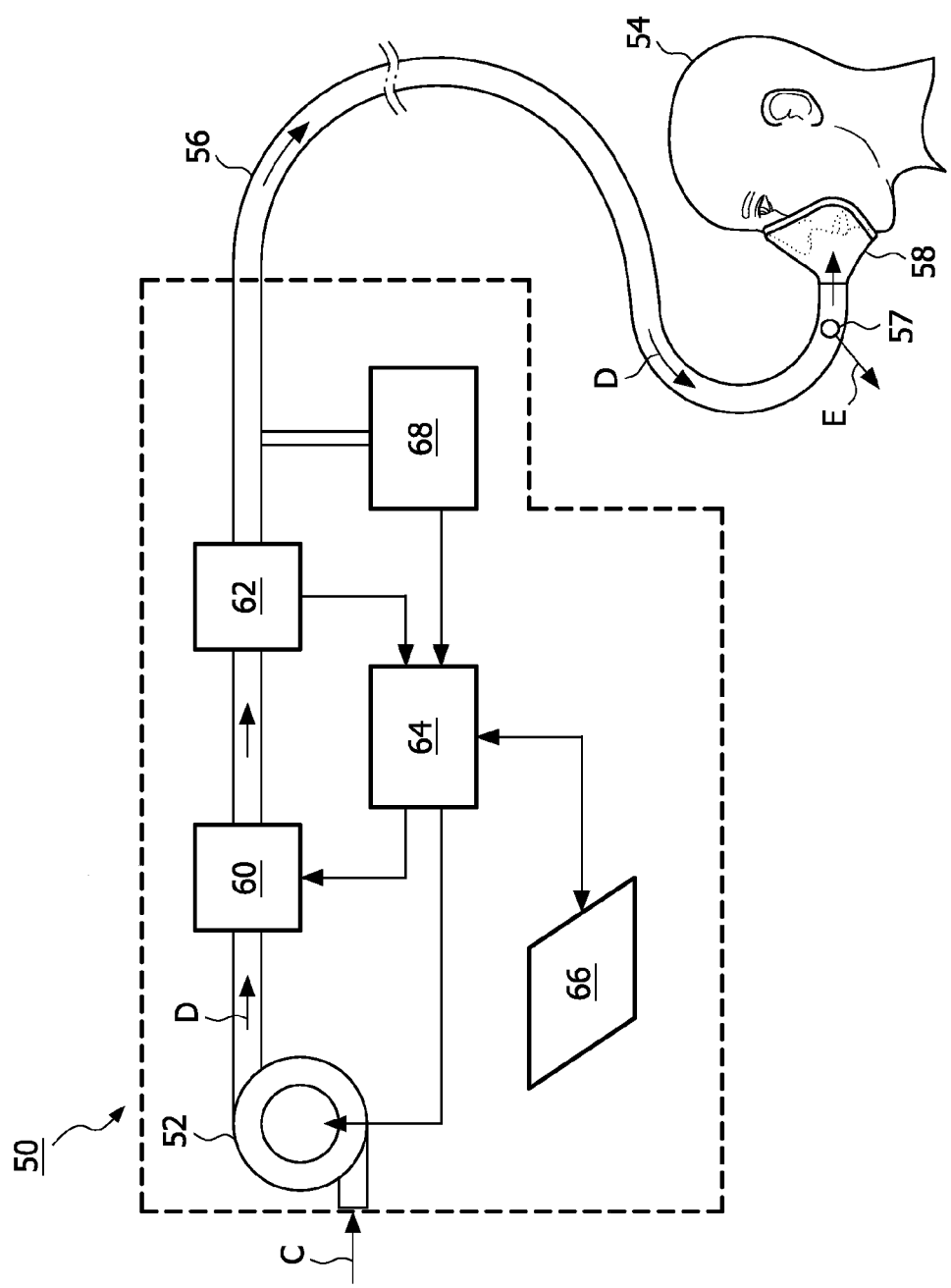
FIG. 1 is a schematic diagram of pressure support system according to one particular, non-limiting embodiment in which the present invention in its various embodiments may be implemented.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As described in greater detail herein, the present invention provides a methodology for automatically titrating the pressure for patients receiving therapy from a pressure support system, particularly where sleep disordered breathing (SDB) presents complex symptoms. The invention as described herein will require less input and decision-making by a physician or technician responsible for supervising therapy and will help to reduce errors in patient treatment. In addition, a pressure support system implementing the methodology as described herein also will be able to continue to treat a patient effectively throughout changes in his or her disease state and will also in most cases result in increased patient comfort.

The present inventors recognized that there are three main independent pieces of information concerning the presentation of sleep disordered breathing that can significantly affect the appropriate titration of a pressure support system on a complicated patient. These three main pieces of information are: (i) airway patency, i.e., the degree to which the patient's airway is open, (ii) the primary cause of the current sleep disordered breathing event, and (iii) the patient's response to previous pressure changes. As described in greater detail herein, the present invention, in an exemplary embodiment, provides a pressure support system wherein the controller for the pressure support system utilizes at least two, and possibly all three, of the three pieces of information described above in order to determine its control response (i.e., control of titration) when presented with a sleep disordered breathing event. Each of the aforementioned pieces of information may be automatically detected by the pressure support system, input by an external device, or could be preset.

FIG. 1 is a schematic diagram of pressure support system 50 according to one particular, non-limiting embodiment in which the present invention in its various embodiments may be implemented. Referring to FIG. 1, pressure support system 50 includes gas flow generator 52, such as a blower used in a conventional CPAP or bi-level pressure support device, which receives breathing gas, generally indicated by arrow C, from any suitable source, e.g., a pressurized tank or source of oxygen or air or other gasses, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure.

In an exemplary embodiment, gas flow generator 52 is capable of providing a flow of breathing gas ranging in pressure form 3-30 cm $H_2O$. The pressurized flow of breathing gas, generally indicated by arrow D from gas flow generator 52, is delivered via delivery conduit 56 to breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 shown in FIG. 1 is what is known as a single-limb system, meaning that the patient circuit includes only delivery conduit 56 connecting patient 54 to pressure support system 50. As such, exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal mask. It is to be understood, however, that patient interface 58 can include a nasal/oral mask, full face mask, nasal cannula, nasal pillows, tracheal tube, endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of valve 60 provided in delivery conduit 56. Valve 60 controls the pressure of the flow of breathing gas from flow generator 52 delivered to patient 54. For present purposes, flow generator 52 and valve 60 are collectively referred to a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. In the particular embodiment shown in FIG. 1, flow sensor 62 is interposed in line with delivery conduit 56, most typically downstream of valve 60. Flow sensor 62 generates a flow signal, $Q_{MEASURED}$, that is provided to controller 64 and is used by controller 64 to determine the flow of gas at patient 54 ($Q_{pt}$). Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Pressure support system 50 also includes pressure sensor 68 operatively coupled to controller 64 that detects the pressure of the gas at patient 54. In the illustrated embodiment, pressure sensor 68 is in fluid communication with patient interface 58 via delivery conduit 56. In this embodiment, the pressure at patient 54 is estimated based on the known pressure drop that occurs in delivery conduit 56. Alternatively, the patient pressure can be measured directly at patient interface 58 using a pressure sensor incorporated therein that is operatively coupled to controller 64.

Controller 64 may be, for example, a microprocessor, a microcontroller or some other suitable processing device, that includes or is operatively coupled to a memory (not shown) that provides a storage medium for data and software executable by controller 64 for controlling the operation of pressure support system 50, including automatically titrating pressure (based on at least two of the three pieces of information described above) when a sleep disordered breathing event is detected as described in greater detail herein.

Finally, input/output device 66 is provided for setting various parameters used by pressure support system 50, as well as for displaying and outputting information and data to a user, such as a clinician or caregiver.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, C-Flex, Bi-Flex, and PPAP are within the scope of the present invention. U.S. Pat. Nos. 5,535,738; 5,794,615; 6,105,575; 6,609,517; and 6,932,084, the contents of each of which are incorporated herein by reference, disclose techniques for providing Flex, Bi-Flex, and PPAP support.

In an exemplary embodiment of the present invention, which is a single-limb system, controller 64 estimates the leakage of gas from the pressure support system using any conventional technique and incorporates this leak estimation into the determination of the actual patient flow. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination.

As noted elsewhere herein, in the exemplary methodology of the present invention (implemented in software executable by controller 64 for controlling pressure support system 50), pressure support system 50 monitors patient 54 in order to detect sleep disordered breathing events, and when such an event is detected, pressure support system 50 automatically titrates the pressure provided to patient 54 based on at least two of the following three pieces of information: (i) airway patency, i.e., the degree to which the patient's airway is open, (ii) the primary cause of the current sleep disordered breathing event, and (iii) the patient's response to previous pressure changes.

In an exemplary embodiment, controller 64 detects sleep disordered breathing events (such as, without limitation, apnea or hypopnea events) by analyzing pressure and flow data provided by pressure sensor 68 and flow sensor 62 (e.g., at a sampling rate of 100 Hz) and using the methodology described in U.S. Pat. No. 7,168,429 to Matthews et al., the disclosure of which is incorporated herein. For the sake of brevity, the details of that methodology are not described in detail herein. It should be appreciated, however, that this is meant to be just one particular embodiment for detecting sleep disordered breathing events, and that other techniques for detecting sleep disordered breathing events may also be employed within the scope of the present invention. For example, an alternative technique for detecting sleep disordered breathing events is described in U.S. Pat. No. 7,118,536 to Haberland et al., the contents of which is incorporated herein by reference.

In addition, a number of particular methods for determining the information relating to (i) airway patency, (ii) the primary cause of the current sleep disordered breathing event, and (iii) the patient's response to previous pressure changes (which are used in the methodology of the present invention) are contemplated. Such particular methods are described in detail elsewhere herein following the description of the automatic titration methods of the various embodiments of the invention that are provided below in connections with FIGS. 2-5. Furthermore, the methods shown in FIGS. 2-5 will, for illustrative purposes, be discussed in connection with and as implemented in pressure support system 50. It should be understood, however, that this is not meant to be limiting, as the methods may be implemented in pressure support systems having different configurations, components and principles of operation.

Figure 2:
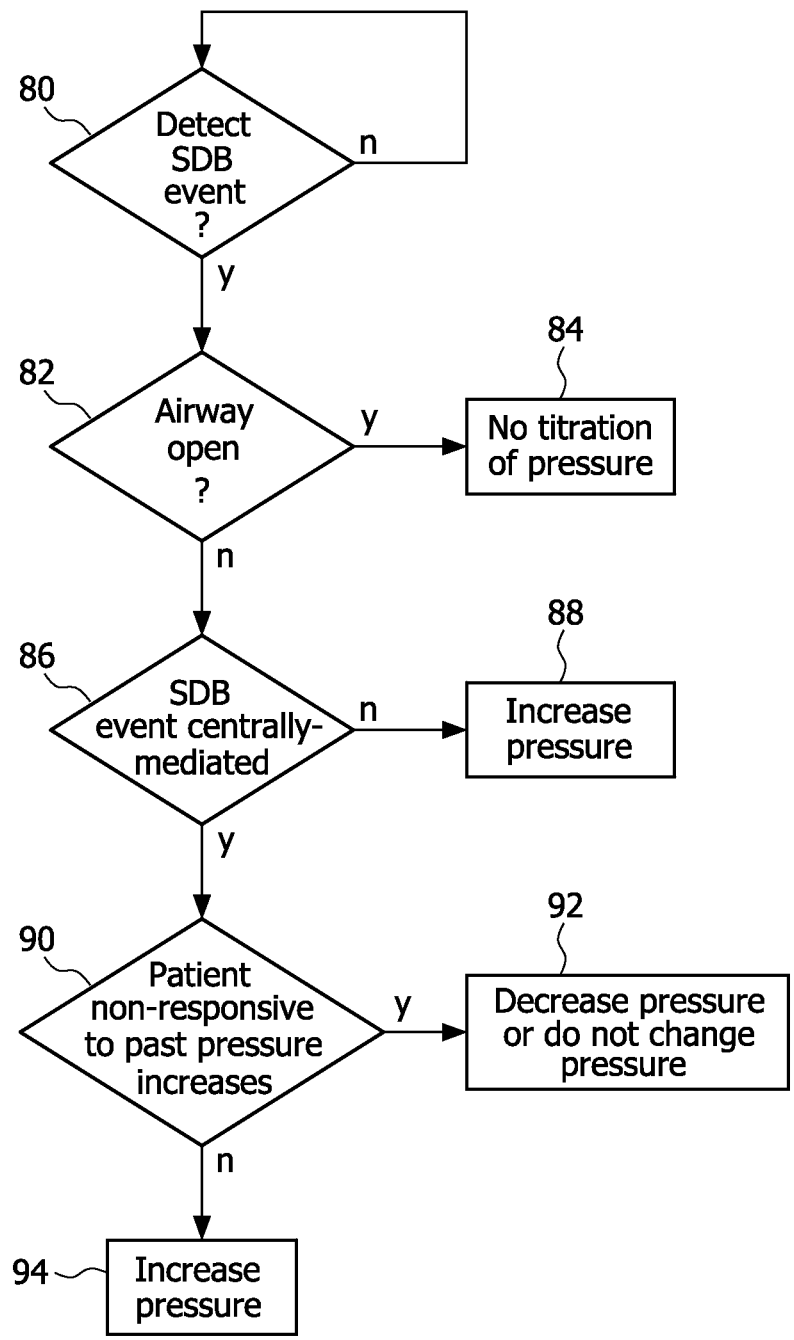
FIG. 2 is a flowchart showing a method of automatically titrating the pressure provided to patient according to a first, non-limiting particular embodiment.

FIG. 2 is a flowchart showing a method of automatically titrating the pressure provided to patient 54 by pressure support system 50 according to a first, non-limiting particular embodiment. In the embodiment shown in FIG. 2, the automatic titration is based on all three of (i) airway patency, (ii) the primary cause of the current sleep disordered breathing event, and (iii) the patient's response to previous pressure changes. The method begins at step 80, wherein a determination is made as to whether an SDB event has been detected using a technique described elsewhere herein or any other suitable technique. If the answer is no, then the method returns to step 80 to await such a detection. If the answer at step 80 is yes, meaning that an SDB event has been detected, then, at step 82, a determination is made as to whether the airway of patient 54 is open. A number of methods for making such a determination are described elsewhere herein.

If the answer at step 82 is yes, meaning the airway of patient 54 is determined to be open, then the method proceeds to step 84 and no titration of pressure is performed. If, however, the answer at step 82 is no, meaning the airway of patient 54 is determined to be closed, then, at step 86, a determination is made as to whether the detected SDB event is considered to be centrally-mediated, meaning that the primary cause of the SDB event is the lack of respiratory drive. A good example of centrally-mediated SDB is a typical Cheyne-Stokes patient. The typical Cheyne-Stokes patient will have apneas every 60-90 seconds in a pattern that is very discernable. The cause of Cheyne-Stokes is known as "central", and is related to the loop gain of the respiratory controller as well as (and primarily) the delay in the respiratory controller loop caused by poor circulation. So, in a Cheyne-Stokes patient or similar patient, even if the patient's airway happens to close completely during the apnea phase, it can be said with some certainty that the apnea is primarily central. A number of methods for making such a determination (i.e., whether an SDB event is centrally-mediated) are described elsewhere herein.

If the answer at step 86 is no, then, at step 88, the pressure provided by pressure support system 50 to patient 54 is increased by a predetermined amount, such as, without limitation 1 cm $H_2O$. In one alternative embodiment, the quantity of the increase may be a function of the current EPAP or CPAP level, and in another alternative embodiment, the quantity of the pressure increase may be a function of the duration of the apnea. If the answer at step 86 is yes, meaning that the detected SDB event is considered to be centrally-mediated, then, at step 90, a determination is made as to whether patient 54 is considered to have been non-responsive to a certain number of previous pressure increases (e.g., over a certain period of time) that have been provided to patient 54 by pressure support system 50. A number of methods for making such a determination are described elsewhere herein.

If the answer at step 90 is yes, meaning that patient 54 is considered to have been non-responsive to previous pressure increases, then, at step 92, either (i) the pressure provided by pressure support system 50 to patient 54 is decreased by a predetermined amount, such as, without limitation, 2 cm $H_2O$, or (ii) the pressure provided by pressure support system 50 to patient 54 is not changed, depending on the circumstances. In one particular embodiment, if patient 54 is determined to be non-responsive, the pressure is decreased for two events while they are non-responsive, and thereafter the pressure is not changed while patient 54 continues to have SDB events while they are non-responsive. After a period of time (e.g. 15 minutes) where the pressure has been "locked down" in this manner, and no SDB events that would typically cause an increase in pressure have occurred, patient 54 may be determined to no longer be "non-responsive". In another alternative embodiment, if the answer at step 90 is yes, meaning that patient 54 is considered to have been non-responsive to previous pressure increases, then the pressure provided by pressure support system 50 to patient 54 is not changed (i.e., it immediately enters the "lock down" mode.

If the answer at step 90 is no, meaning that patient 54 is not determined to have been non-responsive to previous pressure increases (e.g., patient 54 has been responsive or non-responsiveness has not yet been declared), then, at step 94, the pressure provided by pressure support system 50 to patient 54 is increased by a predetermined amount, such as 1 cm $H_2O$.

Figure 3:
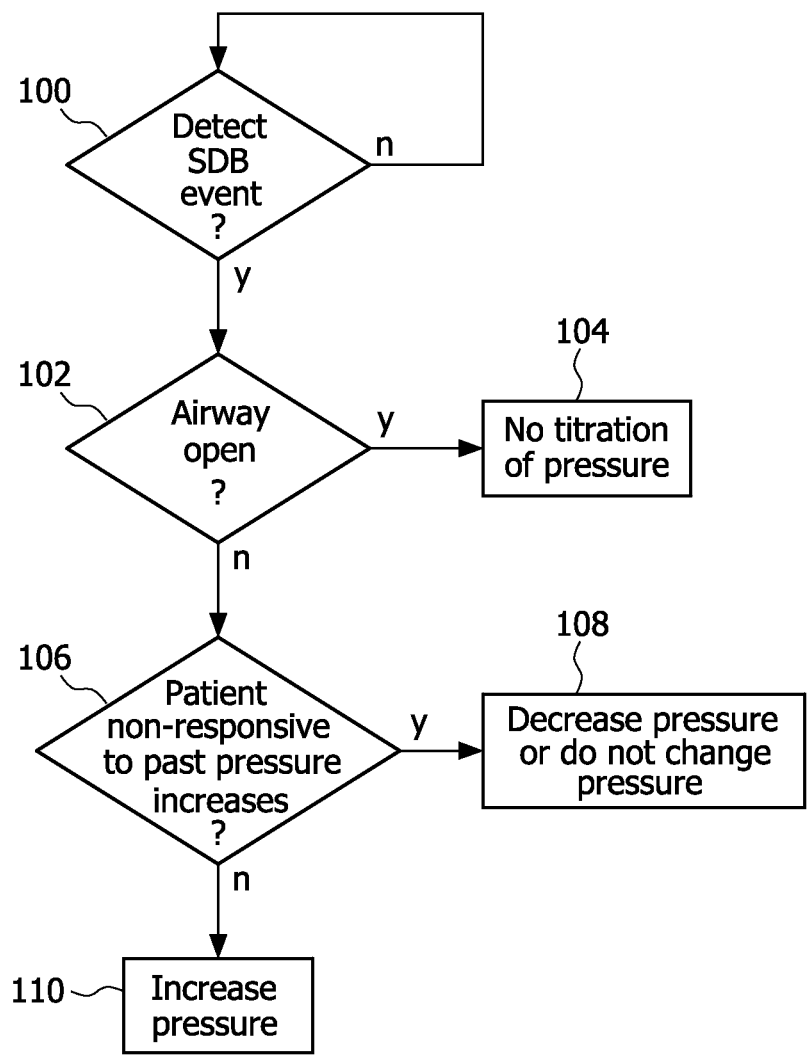
FIG. 3 is a flowchart showing a method of automatically titrating the pressure provided to patient according to a second, non-limiting particular embodiment.

FIG. 3 is a flowchart showing a method of automatically titrating the pressure provided to patient 54 by pressure support system 50 according to a second, non-limiting particular embodiment. In the embodiment shown in FIG. 3, the automatic titration is based only on (i) airway patency and (ii) the patient's response to previous pressure changes. The method begins at step 100, wherein a determination is made as to whether an SDB event has been detected using a technique described elsewhere herein or any other suitable technique. If the answer is no, then the method returns to step 100 to await such a detection. If the answer at step 100 is yes, then, at step 102, a determination is made as to whether the airway of patient 54 is open. A number of methods for making such a determination are described elsewhere herein.

If the answer at step 102 is yes, meaning the airway of patient 54 is determined to be open, then the method proceeds to step 104 and no titration of pressure is performed. If, however, the answer at step 102 is no, meaning the airway of patient 54 is determined to be closed, then, at step 106, a determination is made as to whether patient 54 is considered to have been non-responsive to a certain number of previous pressure increases that have been provided to patient 54 by pressure support system 50. A number of methods for making such a determination are described elsewhere herein. If the answer at step 106 is yes, meaning that patient 54 is considered to have been non-responsive to previous pressure increases, then, at step 108, either (i) the pressure provided by pressure support system 50 to patient 54 is decreased by a predetermined amount, such as 2 cm H$_2$O, or (ii) the pressure provided by pressure support system 50 to patient 54 is not changed. Particular embodiments of this aspect are described elsewhere herein. If, however, the answer at step 106 is no, meaning that patient 54 is not determined to have been non-responsive to previous pressure increases (e.g., patient 54 has been responsive or non-responsiveness has not yet been declared), then, at step 110, the pressure provided by pressure support system 50 to patient 54 is increased by a predetermined amount, such as 1 cm H$_2$O.

Figure 4:
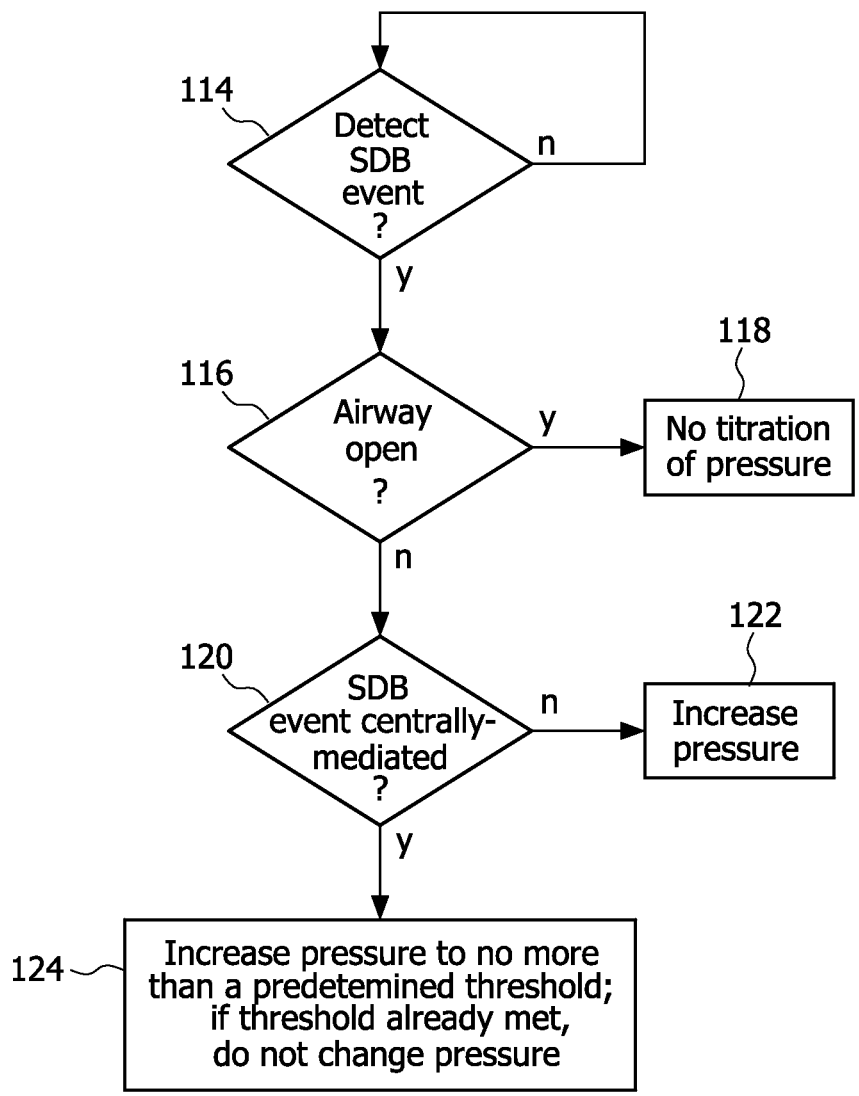
FIG. 4 is a flowchart showing a method of automatically titrating the pressure provided to patient according to a third, non-limiting particular embodiment.

FIG. 4 is a flowchart showing a method of automatically titrating the pressure provided to patient 54 by pressure support system 50 according to a third, non-limiting particular embodiment. In the embodiment shown in FIG. 4, the automatic titration is based only on (i) airway patency and (ii) the primary cause of the current sleep disordered breathing event. The method begins at step 114, wherein a determination is made as to whether an SDB event has been detected using a technique described elsewhere herein or any other suitable technique. If the answer is no, then the method returns to step 114 to await such a detection. If the answer at step 114 is yes, then, at step 116, a determination is made as to whether the airway of patient 54 is open. A number of methods for making such a determination are described elsewhere herein.

If the answer at step 116 is yes, meaning the airway of patient 54 is determined to be open, then the method proceeds to step 118 and no titration of pressure is performed. If, however, the answer at step 116 is no, meaning the airway of patient 54 is determined to be closed, then, at step 120, a determination is made as to whether the detected SDB event is considered to be centrally-mediated. A number of methods for making such a determination are described elsewhere herein. If the answer at step 120 is no, then, at step 122, the pressure provided by pressure support system 50 to patient 54 is increased by a predetermined amount, such as 1 cm H$_2$O. If the answer at step 120 is yes, meaning that the detected SDB event is considered to be centrally-mediated, then, at step 124, the pressure provided by pressure support system 50 to patient 54 is increased by a predetermined amount to no more than a predetermined threshold level, such as 10 cm H$_2$O (a partial increase equal to a portion of the predetermined amount will performed if the entire predetermined amount would cause the threshold to be exceeded). If the predetermined threshold level has already been reached, then no pressure change is made.

Figure 5:
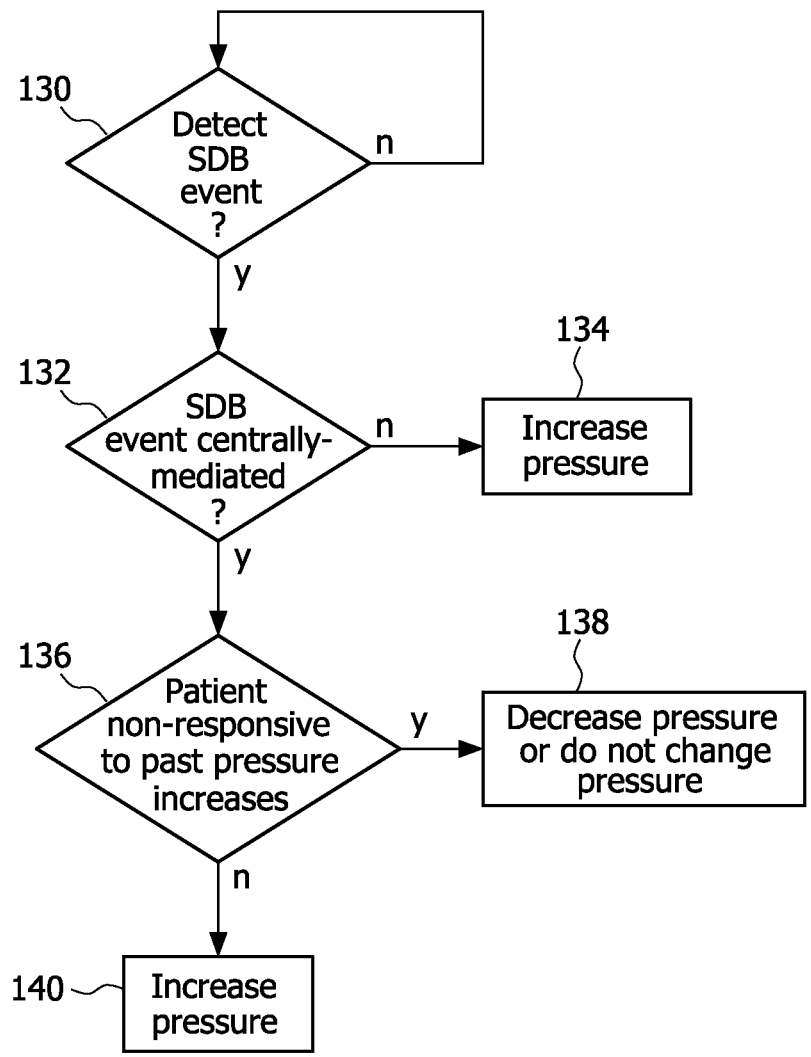
FIG. 5 is a flowchart showing a method of automatically titrating the pressure provided to patient according to a fourth, non-limiting particular embodiment.

FIG. 5 is a flowchart showing a method of automatically titrating the pressure provided to patient 54 by pressure support system 50 according to a fourth, non-limiting particular embodiment. In the embodiment shown in FIG. 5, the automatic titration is based only on (i) the primary cause of the current sleep disordered breathing event, and (ii) the patient's response to previous pressure changes. The method begins at step 130, wherein a determination is made as to whether an SDB event has been detected using a technique described elsewhere herein or any other suitable technique. If the answer is no, then the method returns to step 130 to await such a detection. If the answer at step 130 is yes, then, at step 132, a determination is made as to whether the detected SDB event is considered to be centrally-mediated. A number of methods for making such a determination are described elsewhere herein.

If the answer at step 132 is no, then, at step 134, the pressure provided by pressure support system 50 to patient 54 is increased by a predetermined amount, such as 1 cm H$_2$O. If the answer at step 132 is yes, meaning that the detected SDB event is considered to be centrally-mediated, then, at step 136, a determination is made as to whether patient 54 is considered to have been non-responsive to a certain number of previous pressure increases that have been provided to patient 54 by pressure support system 50. A number of methods for making such a determination are described elsewhere herein. If the answer at step 136 is yes, meaning that patient 54 is considered to have been non-responsive to previous pressure increases, then, at step 138, either (i) the pressure provided by pressure support system 50 to patient 54 is decreased by a predetermined amount, such as 2 cm H$_2$O, or (ii) the pressure provided by pressure support system 50 to patient 54 is not changed. Particular embodiments of this aspect are described elsewhere herein. If, however, the answer at step 136 is no, meaning that patient 54 is not determined to have been non-responsive to previous pressure increases (e.g., patient 54 has been responsive or non-responsiveness has not yet been declared), then, at step 140, the pressure provided by pressure support system 50 to patient 54 is increased by a predetermined amount, such as 1 cm H$_2$O.

As described in detail hereinabove, one of the pieces of information that is employed in various embodiments of the invention is airway patency, i.e., the degree to which the patient's airway is open. There are a number of methods in which airway patency can be determined.

Figure 6:
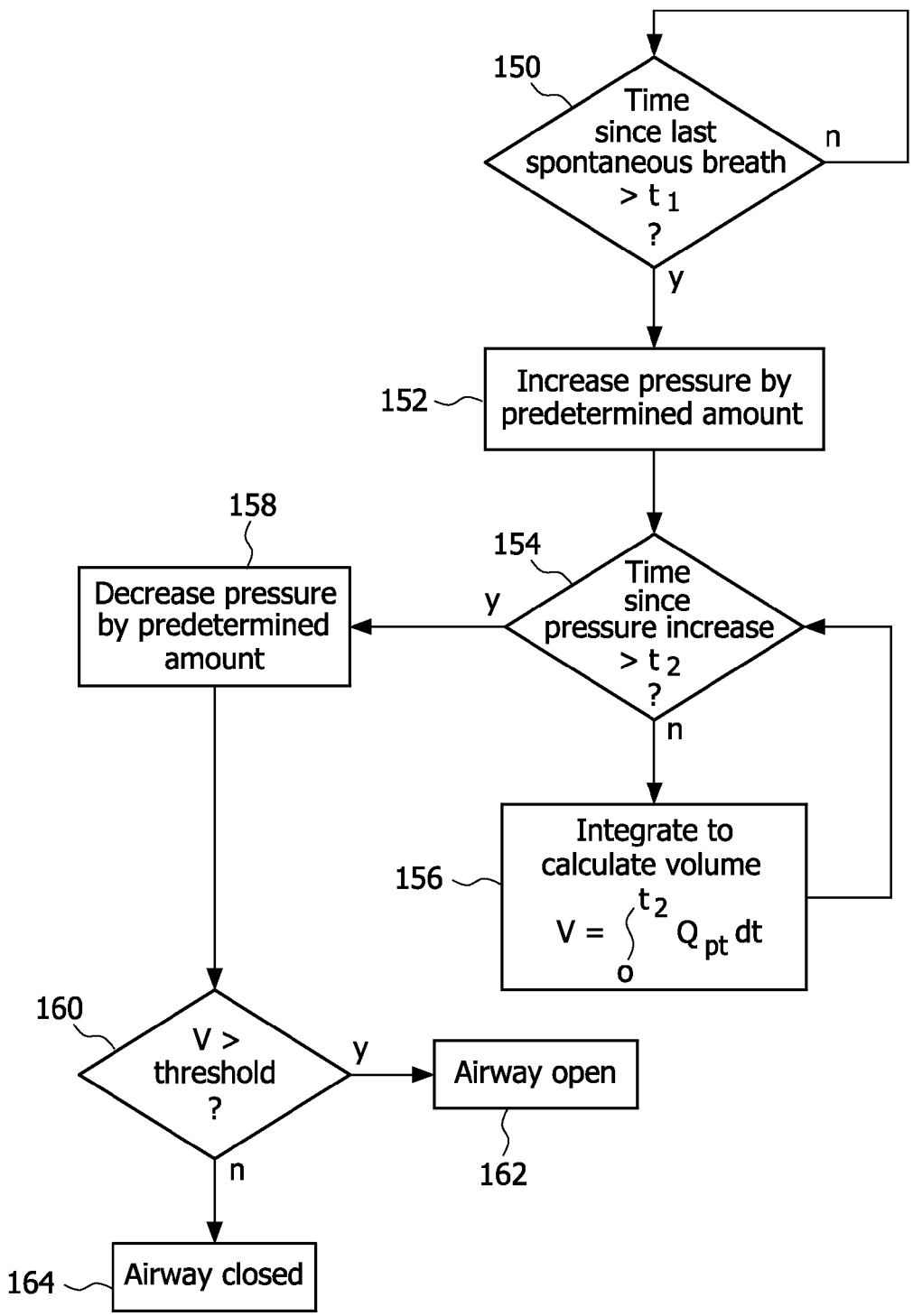
FIG. 6 is a flowchart showing an embodiment of a method for determining airway patency that may be employed in the invention.

According to one particular, exemplary method (a pressure pulse test method), pressure support system 50 waits a period of time and provides a test pressure increase of predetermined amplitude (e.g. 2 cm H$_2$O) and evaluates the degree of flow response to the pressure increase and compares the volume of the flow response to a predetermined threshold. If the amount of volume is greater than the predetermined threshold, then the airway is determined to be open; otherwise, it is determined to be closed. Upon evaluating the flow response, pressure support system 50 decreases the pressure to the prior level. FIG. 6 is a flowchart that shows an implementation of this particular method. The method begins at step 150, wherein a determination is made as to whether the time since the last spontaneous breath is greater than some predetermined time $t_1$. If the answer is no, then the method returns to step 150. If the answer is yes, then, at step 152, pressure support system 50 increase the pressure some predetermined amount, such as 2 cm H$_2$O.

Next, at step 154, a determination is made as to whether the time since the pressure increase is greater than some predetermined time $t_2$. If the answer is no, then, at step 156, volume is calculated by integrating patient flow data (based on data provided by flow sensor 62). Following step 156, the method returns to step 154. If the answer is yes at step 154, then, at step 158, the pressure is decreased by the same predetermined amount, such as 2 cm H$_2$O. Then, at step 160, a determination is made as to whether the calculated volume exceeds some predetermined threshold volume. If the answer is yes, then the airway is deemed to be open (step 162), and if the answer is no, then the airway is deemed to be closed (step 164).

Figure 7:
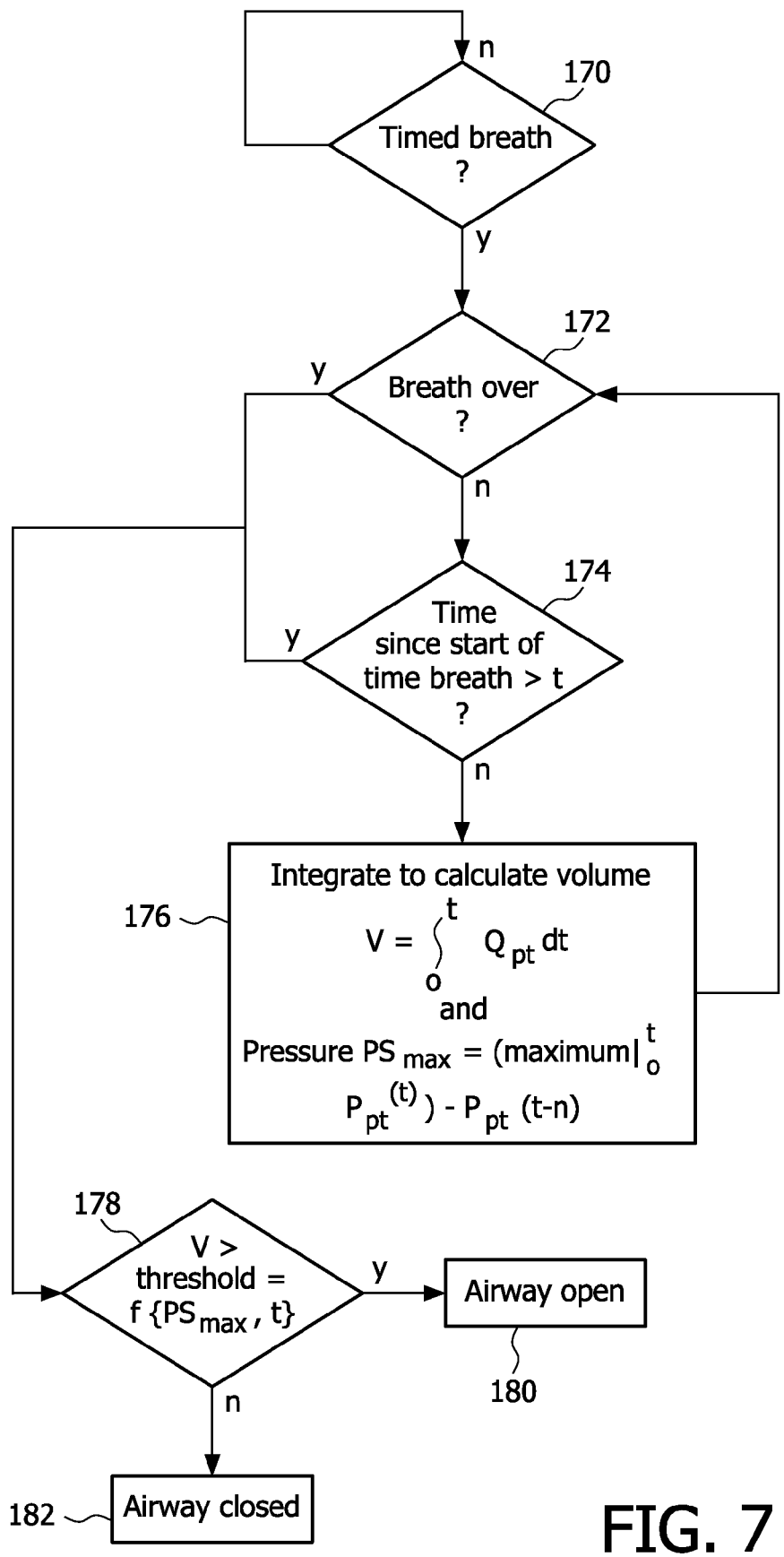
FIG. 7 is a flowchart showing an alternative embodiment of a method for determining airway patency that may be employed in the invention.

According to another particular method, pressure support system 50 provides a pressure increase in response to an independent controller/control operation (e.g. a timed backup breath) with an independently-controlled magnitude (e.g. pressure controlled by an automatic servo ventilator). During the pressure increase, pressure support system 50 measures the flow response, computes the volume of the flow response, and compares it to a threshold that is determined by the magnitude of the pressure increase. If the volume is greater than the threshold, the airway is determined to be open. Otherwise, the airway is closed. Upon evaluating the flow response, pressure support system 50 decreases the pressure to the prior level. FIG. 7 is a flowchart that shows an implementation of this particular method.

The method begins at step 170, wherein a determination is made as to whether a timed breath (also known as a machine breath) has been initiated by pressure support system 50. If the answer is no, then the method returns to step 170. If the answer is yes, then, at step 172, a determination is made as to whether the timed breath is over. If the answer is no, then, at step 174, a determination is made as to whether the time since the initiation of the timed breath is greater than some predetermined time t. If the answer is no, then, at step 176, volume is calculated by integrating patient flow data (based on data provided by flow sensor 62). In addition, a $PS_{max}$ value, which is the maximum pressure achieved within the time t minus the previous end expiratory pressure, is calculated as shown in FIG. 7 ($P_{pt}$ (t−n) is the effective expiratory pressure preceding the timed breath). Following step 176, the method returns to step 172. If the answer at either step 172 or step 174 is yes, then, at step 178, a determination is made as to whether the calculated volume exceeds some predetermined threshold volume which is a function of $PS_{max}$ and time. If the answer is yes, then the airway is deemed to be open (step 180), and if the answer is no, then the airway is deemed to be closed (step 182).

As still another alternative, airway patency can be determined by the well known forced oscillation technique (FOT). The basic premise of FOT is that providing a sinusoidal pressure wave at a known frequency to a patient's airway will generate a corresponding sinusoidal flow wave at the same frequency with amplitude inversely correlated with the resistance of the airway. More specifically, if the airway is open, patient flow will be generated at the same frequency as the provided pressure oscillation, and if the airway is closed, there will no (or very little) patient flow generated in response to the provided pressure oscillation.

Another alternative method is described in U.S. Pat. No. 7,320,320 to Berthon-Jones, the disclosure of which is incorporated herein by reference, which method looks for cardiogenic oscillations during an apnea in order to determine a patent airway. Further alternatives are also possible, such as, without limitation, using a negative pressure test pulse, determining the pressure required to develop a predetermined flow instead of using a preset amount of pressure, and/or using different pressure and flow metrics other than peak pressure and volume, including pressure-time products, mean airflow, mean pressure, etc. Also, an analog or multiple-tier airway state may also be determined and used (e.g. states between fully open and fully closed).

As described in detail hereinabove, another piece of information that is employed in various embodiments of the invention is the primary cause of the current sleep disordered breathing event (and in an exemplary embodiment, whether the event is centrally-mediated). The cause of the current SDB event is determined by information gathered surrounding the event. There are a number of methods for determining the primary cause of the current sleep disordered breathing event. Typically, methods to determine the cause of an event depend upon evaluating a slightly larger segment of data and looking at the time and/or frequency at which a pattern repeats. In an exemplary embodiment, over a certain period of time, such as during the course of the night, pressure support system 50 monitors the time at which SDB events occur and the frequency at which they are occurring. Pressure support system 50 also monitors the fashion in which the SDB event is entered and exited. These inputs can determine the underlying cause of the event (and thus its classification as either centrally-mediated or not) in the manner described below.

Sleep-onset central activity (a centrally-mediated event) is identified by an apnea or repetitive apneas close to the beginning of the night or following an awakening. In an exemplary implementation, pressure support system 50 logs the timing of "awake" events. "Awake" events are events where it can be determined that patient 54 was active and therefore not sleeping. Turning flow generator 52 on at the beginning of the night is one such event, as is changing a parameter on pressure support system 50 (e.g. ramp or comfort setting). Another "awake" event can be determined by the monitoring of the inspired minute ventilation of patient 54. As patient 54 transitions from wake to sleep the inspired minute ventilation will fall to a lower value than during wakefulness. Other "awake" events include, but are not limited to: large arousal breaths, drastic changes in mask leak, inspiration followed by a hold before expiration, etc. When pressure support device detects an apnea event, it compares the time at which the apnea event occurred to the last previous "awake" event. If the time is shorter than a predetermined amount (e.g. 3 minutes), then it is determined that the event was likely a sleep-onset central activity.

Cheyne-Stokes Respiration (a centrally-mediated event that is described in greater detail elsewhere herein) can be determined by the frequency at which apneas or hypopneas are occurring as well as by the classic waxing-waning profile. In an exemplary embodiment, the peak flows of breaths and the timing of the breaths are recorded. The peak flows are then compared to a template corresponding to CSR (e.g. triangle wave) and the degree of modulation (e.g. max-min comparison) of the peak flows is recorded as well as the frequency of the modulation (e.g. peak-to-peak or trough-to-trough time) is recorded. If the correlation to the template is greater than a predetermined amount (e.g. 80%) and the modulation is greater than a predetermined amount (e.g. 50%) and if the modulation time is within a preset range (e.g. 30-90 seconds) and the duration of the disturbance has persisted for at least 2 cycles, it is determined that patient 54 is experiencing CSR. This method is described in greater detail in U.S. patent application Ser. No. 11/235,520 to Kane et al., which is now U.S. Pat. No. 7,717,110 granted on May 18, 2010, the disclosure of which is incorporated herein by reference. In another embodiment, the minute ventilation signal is monitored for oscillations occurring at 30-90 seconds. If the oscillations persist for more than a predetermined number of cycles (e.g. two) and if the oscillations are of sufficient magnitude (e.g. 2 Liters), then it is determined that patient 54 is experiencing CSR. The minute ventilation signal can be determined in a number of different ways known to those skilled in the art.

Opioid-induced central activity (a centrally-mediated event) is identified by the frequency at which apneas are occurring as well as abrupt entry and exit to the apneas. In an exemplary embodiment, the peak flows of breaths and the timing of the breaths are recorded. If the peak flows show relative consistency (e.g. +/−5 LPM) while the timing of the breaths is sporadic and includes a number of pauses of significant lengths (e.g. greater than or equal to eight seconds), it is determined that patient 54 has opioid-induced central activity. In another embodiment, the frequency of apneas and hypopneas are recorded, and if apneas and hypopneas are occurring at a rate equal or greater than a predetermined rate (e.g. two per minute), it is determined that patient 54 is experiencing opioid-induced central activity.

Primary obstructive apneas (not centrally-mediated events) are identified by irregular timing of apneas as well as typically gradual entry and abrupt exit. In an exemplary implementation, the peak flows of the breaths and the timing of the breaths are recorded. If the peak flows show a gradual entry into an apnea or hypopnea event followed by an abrupt exit, then it is determined that the event is a primary obstructive event. In another embodiment, the SDB event is determined to be likely to be obstructive if the event is not classified as a different type of central event.

Furthermore, other signals derived from the airflow delivered to patient 54 aside from peak airflow can be used in order to determine the event type including, but not limited to: tidal volume, mean airflow, minute ventilation, frequency domain measurements of the airflow, etc. In addition, other signals derived from different sources can be used to determine or augment evaluation of event types, such as signals from pressure sensor 68, an ECG, an accelerometer, etc. Still further methods for determining the cause of an SDB event are possible, such as, without limitation, using external sensors in the environment where pressure sensing system 50 is being used (e.g., a bedroom), on patient interface 58, or on patient 54, using an ECG to look for Cheyne-Stokes Respiration, using $SpO_2$ to look for rhythmic changes in blood gas concentrations, and using frequency-domain techniques (FFT, wavelet, time-frequency, etc.) in order to match an appropriate frequency-domain representation of a given cause.

As described in detail hereinabove, the last piece of information that is employed in various embodiments of the invention is the patient's response to previous pressure changes. The concept of monitoring the patient's response to pressure changes is important because it can provide useful information predicting the patient's response to future pressure changes. In an exemplary embodiment, pressure support system 50 records and analyzes the response of patient 54 to previous pressure changes. Specifically, in this implementation, pressure support system 50 monitors whether successive pressure changes have occurred without resolving apnea events or whether pressure changes have caused apnea events to turn into hypopnea events. Pressure support system 50 also records the frequency at which the SDB events are occurring and the frequency at which pressure changes have occurred.

Recording of the response of patient 54 to changes in the therapy pressure allows pressure support system 50 to determine whether SDB events of patient 54 are being treated by the changes in therapy. If the SDB events of patient 54 are not responsive to the therapy pressure increases and continue to occur, then it is likely that future pressure increases are not desirable. Cases in which this can occur include cases where pressure support system 50 increases titration pressure in response to centrally-mediated apneas and cases in which central apneas are accompanied by active laryngeal closure.

To determine the response of patient 54 to events, the pressure at which an apnea is detected is recorded. A threshold is set at 3 cm $H_2O$ above the current pressure at which the apnea is recorded. If the pressure is increased in response to successive apneas to the threshold, then it is determined that the SDB events of patient 54 are not responding to the increase in therapy pressure and the responsiveness state of patient 54 is set to "non-responsive." If however, the SDB events of patient 54 convert from apneas to hypopneas or to snoring, then a new threshold is set and the patient is considered "responsive." Also, if patient 54 does not have any SDB events for a predetermined amount of time after the pressure increase, then the threshold is reset and the patient is considered "responsive." This method is described in greater detail in U.S. Pat. No. 7,168,429 to Matthews et al., the disclosure of which is incorporated herein by reference.

Alternative methods for determining patient response to pressure increases include instead of using a hard threshold, tracking the patient response over time to pressure increases, using the number of pressure increases over time instead of using a pressure threshold, determining an analog scale of "responsiveness" (as opposed to merely response or non-responsive), and using pressure-dependant tracking or changing the sensitivity of the tracking as the pressure changes.

Thus, the present invention incorporates a comprehensive titration scheme that takes into account the most pertinent information concerning the SDB event to which it is responding. Current technology either only monitors the airway state or monitors the patient's response to successive pressure increases. Accordingly, unnecessary pressure increases can occur when only monitoring the airway state, responding to successive closed airway centrals. Similarly, unnecessary pressure increases can occur when only monitoring the responsiveness of a patient to pressure increases, increasing pressure to open airway central apneas in order to determine that the patient has not responded to the pressure increases.

The current invention maximizes the probability of successful treatment of SDB patients through taking a comprehensive look at any given SDB event and maximizing the probability of successful titration. Unnecessary pressure increases will be minimized and the most complicated patients, including those with OSA and CSA, will be able to be treated effectively. The present invention is optimized for titration of all pressure support devices, including, but not limited to BiPAP AutoSV, Auto CPAP, BiPAP Auto, volume-based systems, AVAPS, and BiPAP S/T.

In an alternative embodiment, pressure may be automatically titrated based solely on the primary cause of the sleep disordered breathing event. Thus, according to such an embodiment, a method of providing pressure support to patient 54 includes detecting the occurrence of a sleep disordered breathing event in patient 54, in a manner described elsewhere herein or using any suitable technique, and, in response to detecting the SDB event, titrating the pressure of the flow of gas provided to patient 54 by pressure support system 50 based on the determined cause of the sleep disordered breathing event. Preferably, this method includes determining whether the sleep disordered breathing event is centrally-mediated, wherein the titrating step includes titrating the pressure in a first manner, such as not changing the pressure (or not increasing the pressure above a preset threshold e.g. 10 cm H2O), if the sleep disordered breathing event is determined to be centrally-mediated and titrating the pressure in a second manner different than the first manner, such as increasing the pressure (e.g. 1 cm H2O), if the sleep disordered breathing event is determined to not be centrally-mediated.

It can thus be appreciated that the present invention provides an auto-titrating pressure support system that effectively treat patients that are regarded as complex for effectively than current system. More specifically, the present invention provides an improved methodology for automating the difficult process of titrating EPAP (or CPAP on an AutoCPAP device) on a complex patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing pressure support to a patient, comprising:
   detecting an occurrence of a sleep disordered breathing event in the patient; and
   in response to the detecting, titrating a pressure of a flow of gas provided to the patient based (i) on
      a determined patency of an airway of the patient, the patency being determined (a) by:
         providing a test pressure titration to the patient over a first time period;
         measuring a flow response to the test pressure titration over the first time period; and
         comparing a first volume of the flow response to a first volume threshold,
      or (b) by:
         calculating a maximum pressure support (PS) pressure by subtracting an effective expiratory pressure preceding a timed breath from a maximum pressure achieved by the patient within a second time period; and
         comparing a second volume of the gas flow of the patient over the timed breath of over the second time period to a second volume threshold that is a function of the maximum PD pressure and the second time period,
   and (ii) on:
      (a) a determined cause of the sleep disordered breathing event, and/or
      (b) a determined responsiveness of the patient to previous pressure changes in the flow of gas provided to the patient.

2. The method of claim 1, the method further comprising, in response to the detecting, determining the determined patency of the airway of the patient by:
   providing the test pressure titration with an independently-controlled amplitude to the patient,
   computing the first volume of the flow response to the test pressure titration,
   comparing the first volume to the first volume threshold that is determined by the amplitude of the test pressure titration, and
   determining whether the airway is closed based on the comparison.

3. The method of claim 1, wherein the cause is determined based on:
   a time at which the sleep disordered breathing event occurred relative to a course of a night slept by the patient,
   a frequency at which the sleep disordered breathing event is occurring, and/or
   an irregular timing of the sleep disordered breathing event that is gradually entered and abruptly exited.

4. The method of claim 1, wherein the responsiveness is determined based on successive occurrences of the sleep disordered breathing event notwithstanding the previous pressure changes resulting in a pressure of the flow of gas that reaches or breaches a pressure threshold relative to the pressure at which the sleep disordered breathing event is detected and based on the sleep disordered breathing event down-converting in response to the previous pressure changes where the pressure of the flow of gas did not reach or breach the pressure threshold.

5. A method of providing pressure support to a patient, comprising:
   detecting an occurrence of a sleep disordered breathing event in the patient; and
   in response to the detecting, titrating a pressure of a flow of gas provided to the patient based (i) on:
      a determined cause of the sleep disordered breathing event, the cause being determined based on:
         a time at which the sleep disordered breathing event occurred relative to a course of a night slept by the patient,
         a frequency at which the sleep disordered breathing event is occurring, and/or
         an irregular timing of the sleep disordered breathing event that is gradually entered and abruptly exited,
   and (ii) on:
      (a) a determined patency of an airway of the patient, and/or
      (b) a determined responsiveness of the patient to previous pressure changes in the flow of gas provided to the patient.

6. The method of claim 5,
   wherein the patency is determined (a) by:
      providing a test pressure titration to the patient over a first time period;
      measuring a flow response to the test pressure titration over the first time period; and
      comparing a first volume of the flow response to a first volume threshold,
   or (b) by:
      calculating a maximum pressure support (PS) pressure by subtracting an effective expiratory pressure preceding a timed breath from a maximum pressure achieved by the patient within a second time period; and
      comparing a second volume of the gas flow of the patient over the timed breath or over the second time period to a second volume threshold that is a function of the maximum PS pressure and the second time period.

7. The method of claim 5, wherein the responsiveness is determined based on successive occurrences of the sleep disordered breathing event notwithstanding the previous pressure changes resulting in a pressure of the flow of gas that reaches or breaches a pressure threshold relative to the pressure at which the sleep disordered breathing event is detected and based on the sleep disordered breathing event down-converting in response to the previous pressure changes where the pressure of the flow of gas did not reach or breach the pressure threshold.

8. A method of providing pressure support to a patient, comprising:
  detecting an occurrence of a sleep disordered breathing event in the patient; and
  in response to the detecting, titrating a pressure of a flow of gas provided to the patient based (i) on:
    a determined responsiveness of the patient to previous pressure changes in the flow of gas provided to the patient, the responsiveness being determined based on successive occurrences of the sleep disordered breathing event notwithstanding the previous pressure changes resulting in a pressure of the flow of gas that reaches or breaches a pressure threshold relative to the pressure at which the sleep disordered breathing event is detected and based on the sleep disordered breathing event down-converting in response to the previous pressure changes where the pressure of the flow of gas did not reach or breach the pressure threshold,
  and (ii) on:
    (a) a determined patency of an airway of the patient, and/or
    (b) a determined cause of the sleep disordered breathing event.

9. The method of claim 8,
wherein the patency is determined (a) by:
  providing a test pressure titration to the patient over a first time period;
  measuring a flow response to the test pressure titration over the first time period; and
  comparing a first volume of the flow response to a first volume threshold,
or (b) by:
  calculating a maximum pressure support (PS) pressure by subtracting an effective expiratory pressure preceding a timed breath from a maximum pressure achieved by the patient within a second time period; and
  comparing a second volume of the gas flow of the patient over the timed breath or over the second time period to a second volume threshold that is a function of the maximum PS pressure and the second time period.

10. The method of claim 8, wherein the cause is determined based on:
  a time at which the sleep disordered breathing event occurred relative to a course of a night slept by the patient,
  a frequency at which the sleep disordered breathing event is occurring, and/or
  an irregular timing of the sleep disordered breathing event that is gradually entered and abruptly exited.

* * * * *